United States Patent
Zhang (10) Patent No.: US 11,216,475 B2
(45) Date of Patent: Jan. 4, 2022

(54) METHOD AND SYSTEM FOR AUTOMATICALLY DISCOVERING INFERENCE RULE, DATABASE AND RETRIEVAL METHOD

(71) Applicant: BOE TECHNOLOGY GROUP CO., LTD., Beijing (CN)

(72) Inventor: Zhenzhong Zhang, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 228 days.

(21) Appl. No.: 16/317,686

(22) PCT Filed: Jan. 17, 2018

(86) PCT No.: PCT/CN2018/073004
§ 371 (c)(1),
(2) Date: Jan. 14, 2019

(87) PCT Pub. No.: WO2019/000920
PCT Pub. Date: Jan. 3, 2019

(65) Prior Publication Data
US 2019/0171642 A1  Jun. 6, 2019

(30) Foreign Application Priority Data
Jun. 28, 2017  (CN) .................. 201710507636.9

(51) Int. Cl.
*G06F 16/2458*  (2019.01)
*G06F 16/28*  (2019.01)
(Continued)

(52) U.S. Cl.
CPC ........ *G06F 16/2465* (2019.01); *G06F 16/288* (2019.01); *G06N 5/04* (2013.01);
(Continued)

(58) Field of Classification Search
None
See application file for complete search history.

(56) References Cited

U.S. PATENT DOCUMENTS

| 2008/0201280 A1 | 8/2008 | Martin et al. |
| 2012/0060216 A1* | 3/2012 | Chaudhri ............... G16H 70/00 726/21 |

(Continued)

FOREIGN PATENT DOCUMENTS

| CN | 106528609 A | 3/2017 |
| CN | 106528610 A | 3/2017 |
| CN | 106874695 A | 6/2017 |

OTHER PUBLICATIONS

Shi et al., Semantic Health Knowledge Graph: Semantic Integrations of Heterogeneous Medical Knowledge and Services, Feb. 2017 (Year: 2017).*

(Continued)

*Primary Examiner* — Dawaune A Conyers
(74) *Attorney, Agent, or Firm* — Broooks Kushman P.C.

(57) ABSTRACT

The disclosure provides a method and a system for automatically discovering an inference rule, a medical knowledge database and a retrieval method. The method includes: acquiring a relation matrix for each medical relation, the relation matrix representing a relationship between vectors of the medical entities having the medical relation; and acquiring the inference rules based on the relation matrices for the plurality of medical relations, each inference rule including a first medical relation, a second medical relation and a third medical relation, the inference rule representing that the third medical relation is inferred from the first medical relation and the second medical relation.

17 Claims, 5 Drawing Sheets

(51) Int. Cl.
G06F 17/16 (2006.01)
G16H 50/70 (2018.01)
G06N 5/04 (2006.01)

(52) U.S. Cl.
CPC ............ *G16H 50/70* (2018.01); *G06F 17/16* (2013.01); *G06F 2216/03* (2013.01)

(56) References Cited

U.S. PATENT DOCUMENTS

| | | | |
|---|---|---|---|
| 2013/0066870 A1 | 3/2013 | Somasundaran et al. | |
| 2014/0344213 A1 | 11/2014 | Kent et al. | |
| 2015/0019462 A1 | 1/2015 | De et al. | |
| 2016/0042134 A1* | 2/2016 | Takla | G06F 16/3322 705/3 |
| 2018/0067981 A1* | 3/2018 | Ahuja | G06F 16/9024 |
| 2020/0302117 A1* | 9/2020 | Hu | G16H 50/70 |

OTHER PUBLICATIONS

First Office Action for Chinese Application No. 201710507636.9, dated Apr. 13, 2020, 8 Pages.
Extended European Search Report for Application No. EP 18824315.8, dated Mar. 11, 2020, 9 Pages.
Lin et al., "Learning Entity and Relation Embedding for Knowledge Graph Completion," Proceedings of the 29th Association for the Advancement of Artificial Intelligence Conference, 2015, pp. 2181-2187, (7 Pages).
Chen et al., "Rule-Augmented Representation Learning Approach in Knowledge Graph," CNKI Journal of Technology Intelligence Engineering, Mar. 1, 2017, Department of Computer Science and Technology, Zhejiang University, Hangzhou, China, 9 pages.
1st Chinese Office Action, English Translation.
CN106528609A, English Abstract and Machine Translation.
CN106528610A, English Abstract and Machine Translation.
CN106874695A, English Abstract and Machine Translation.
Non-patent literature reference entitled, "Rule-Augmented Representation Learning Approach in Knowledge Graph", English Abstract and Machine Translation.
Second Office Action for Chinese Application No. 201710507636.9, dated Nov. 18, 2020, 8 Pages.
Toutanova et al., "Compositional Learning of Embeddings for Relation Paths in Knowledge Base and Text," Proceedings of the 54th Annual Meeting of the Association for Computational Linguistics, Aug. 2016, 1434-1444, vol. 1: Long Papers, Association for Computational Linguistics, Berlin, Germany, 11 Pages.
First Office Action for Japanese Application No. 2019-569383, dated Aug. 18, 2021, 4 Pages.
Yang et al., "Embedding Entities and Relations for Learning and Inference in Knowledge Bases," Computer Science Conference ICLR, Aug. 1, 20158, arXiv:1412.6575v4, Cornell University, Internet <URL:https://arxiv.org/pdf/1412.6575.pdf>, 12 Pages.

\* cited by examiner

METHOD AND SYSTEM FOR AUTOMATICALLY DISCOVERING INFERENCE RULE, DATABASE AND RETRIEVAL METHOD

CROSS-REFERENCE TO RELATED APPLICATIONS

This application is the U.S. national phase of PCT Application No. PCT/CN2018/073004 filed on Jan. 17, 2018, which claims priority to Chinese Patent Application No. 201710507636.9 filed on Jun. 28, 2017, which are incorporated herein by reference in their entireties.

TECHNICAL FIELD

The present disclosure relates to the field of data mining from a medical knowledge base, in particular to a method and a system for automatically discovering an inference rule, a medical knowledge database, and a retrieval method.

BACKGROUND

Currently, the number of biomedical publications has grown exponentially. Although with more information, it is difficult for researchers to discover association information among different publications, so the researchers may lose a chance to discover some important knowledge. For example, in the biomedical domain, there are currently more than twenty million theses in a biomedical literature database MEDLINE, with millions of theses being added thereinto every year. It is very difficult for the researchers to read such a huge amount of theses. Hence, there is an urgent need to provide a method for automatic discovery of knowledge from the medical literature.

SUMMARY

An embodiment of the present disclosure provides a method and a system for automatically discovering an inference rule, a medical knowledge database established on the basis of the inference rule, and a retrieval method.

Some embodiment of the present disclosure provides a method for automatically discovering an inference rule for use in a medical knowledge base, the medical knowledge base including a plurality of medical knowledges, each medical knowledge comprising two medical entities and one medical relation between the two medical entities, the method including: acquiring a relation matrix for each medical relation, the relation matrix representing a relationship between vectors of the medical entities having the medical relation; and acquiring the inference rules in accordance with the relation matrices for the plurality of medical relations, each inference rule including a first medical relation, a second medical relation and a third medical relation, the inference rule representing that the third medical relation is inferred from the first medical relation and the second medical relation.

In an alternative embodiment of the present disclosure, the acquiring the relation matrix for each medical relation includes: creating an initial relation matrix for each medical relation; acquiring a medical knowledge corresponding to the medical relation in the medical knowledge base as a correct medical knowledge; changing a medical entity in the correct medical knowledge to acquire a new medical knowledge as a wrong medical knowledge; scoring the correct medical knowledge and the wrong medical knowledge using a scoring function; and performing a learning operation on the initial relation matrix using a predetermined target function, so that a score of the correct medical knowledge is higher than a score of the wrong medical knowledge, acquiring the relation matrix for the medical relation.

In an alternative embodiment of the present disclosure, a difference between the number of the correct medical knowledges and the number of the wrong medical knowledges is smaller than a predetermined threshold when the learning operation is performed on the initial relation matrix.

In an alternative embodiment of the present disclosure, the changing the medical entity in the correct medical knowledge so as to acquire the new medical knowledge as the wrong medical knowledge includes replacing the medical entity in the correct medical knowledge with a medical entity other than medical entities in all the correct medical knowledges corresponding to the medical relation, so as to acquire the new medical knowledge as the wrong medical knowledge.

In an alternative embodiment of the present disclosure, prior to acquiring the relation matrix for each medical relation, the method further includes: acquiring a one-hot code vector for each medical entity through the following formula $$x_e = (a_1, \ldots, a_i, \ldots, a_N), a_j = \begin{cases} 1, \text{ if } j = i \\ 0, \text{ if } j \neq i \end{cases},$$

where N represents the number of the medical entities in the medical knowledge base, and $x_e$ represents a vector in $N*1$ dimensions; and acquiring a vector of each medical entity in accordance with the one-hot code vector for each medical entity through the following formula $y_e = \sigma(Wx_e)$, $\sigma(x) = 1/(1+e^x)$, where $y_e$ represents a vector in $K*1$ dimensions, W represents a mapping matrix and is a vector in $K*N$ dimensions, and K is a predetermined value smaller than N.

In an alternative embodiment of the present disclosure, the scoring function is $\text{Score}(r(e_1, e_2)) = y_{e_1}^T M_r y_{e_2}$, where r represents the medical relation, $e_1$ and $e_2$ represent the medical entities, $r(e_1, e_2)$ represents the medical knowledge, $\text{Score}(\bullet)$ represents the scoring function, and $M_r$ represents the relation matrix for the medical relation r.

In an alternative embodiment of the present disclosure, the predetermined target function is:

$$L = \sum_{r(e_1,e_2)\in T} \sum_{r(e'_1,e'_2)\in T'} \max\{\text{Score}(r(e'_1, e'_2)) - \text{Score}(r(e_1, e_2)) + 1, 0\},$$

where L represents the target function, T represents a set of the correct medical knowledges, T' represents a set of the wrong medical knowledges, and $M_r$ represents the relation matrix for the medical relation r.

In an alternative embodiment of the present disclosure, the acquiring the inference rule in accordance with the relation matrix for the medical relation includes: selecting a plurality of groups of medical relations from all the medical relations, and creating a plurality of to-be-validated inference rules, each of the plurality of to-be-validated inference rule corresponding to one group of medical relations, each group of medical relations including three medical relations; calculating a similarity between a product of relation matrices for two medical relations in each group of medical relations and a relation matrix for the other medical relation in the group of medical relations; and selecting parts of the to-be-validated inference rules as the final inference rules in accordance with the similarities.

In an alternative embodiment of the present disclosure, the selecting the parts of the to-be-validated inference rules as the final inference rules in accordance with the similarities includes: ranking the similarities corresponding to all the groups of medical relations and obtaining a predetermined number of to-be-validated inference rules having the largest similarity; and determining the predetermined number of to-be-validated inference rules having the largest similarity as the final inference rules.

In an alternative embodiment of the present disclosure, the three medical relations in each group of medical relations meet the following conditions: (1) $L_p \cap H_q \neq \emptyset$, (2) $H_p \cap H_r \neq \emptyset$ and (3) $L_q \cap r_r \neq \emptyset$, where $H_p$, $H_q$ and $H_r$ represent sets of all first medical entities in triplets corresponding to the three medical relations p, q and r in the group of medical relations respectively, and $L_p$, $L_q$ and $L_r$ represent sets of all second medical entities in the triplets corresponding to the three medical relations p, q and r in the group of medical relations respectively.

In an alternative embodiment of the present disclosure, the calculating the similarity between the product of the relation matrices for two medical relations in each group of medical relations and the relation matrix for the other medical relation in the group of medical relations includes calculating an L2 norm between the product of the relation matrices for two medical relations in each group of medical relations and the relation matrix for the other medical relation in the group of medical relations as the similarity.

In another aspect, the present disclosure provides in some embodiments a system for automatically discovering an inference rule for use in a medical knowledge base, the medical knowledge base including a plurality of medical knowledges, each medical knowledge comprising two medical entities and one medical relation, the system including: a relation matrix learner configured to acquire a relation matrix for each medical relation, the relation matrix representing a relationship between vectors of the medical entities having the medical relation; and an inference rule finder configured to acquire the inference rules in accordance with the relation matrices for the plurality of medical relations, each inference rule including a first medical relation, a second medical relation and a third medical relation, the inference rule representing that the third medical relation is inferred from the first medical relation and the second medical relation.

In an alternative embodiment of the present disclosure, the relation matrix learner is further configured to: create an initial relation matrix for each medical relation; acquire a medical knowledge corresponding to the medical relation in the medical knowledge base as a correct medical knowledge; change a medical entity in the correct medical knowledge so as to acquire a new medical knowledge as a wrong medical knowledge; score the correct medical knowledge and the wrong medical knowledge using a scoring function; and perform a learning operation on the initial relation matrix using a predetermined target function, so as to enable a score of the correct medical knowledge is higher than a score of the wrong medical knowledge, thereby to acquire the relation matrix for the medical relation.

In an alternative embodiment of the present disclosure, a difference between the number of the correct medical knowledges and the number of the wrong medical knowledges is smaller than a predetermined threshold when the learning operation is performed on the initial relation matrix.

In an alternative embodiment of the present disclosure, the relation matrix learner is further configured to replace the medical entity in the correct medical knowledge with a medical entity other than medical entities in all the correct medical knowledges corresponding to the medical relation, so as to acquire the new medical knowledge as the wrong medical knowledge.

In an alternative embodiment of the present disclosure, the system further includes an entity vector learner configured to: acquire a one-hot code vector for each medical entity through the following formula $$x_e = (a_1, \ldots, a_i, \ldots, a_N), a_j = \begin{cases} 1, \text{if } j = i \\ 0, \text{if } j \neq i \end{cases},$$

where N represents the number of the medical entities in the medical knowledge base, and $x_e$ represents a vector in N*1 dimensions; and acquire a vector of each medical entity in accordance with the one-hot code vector of the medical entity through the following formula $y_e = \sigma(Wx_e)$, where $\sigma(x) = 1/(1+e^x)$, where $y_e$ represents a vector in K*1 dimensions, W represents a mapping matrix and is a vector in K*N dimensions, and K is a predetermined value smaller than N.

In an alternative embodiment of the present disclosure, the scoring function is $\text{Score}(r(e_1, e_2)) = y_{e_1}^T M_r y_{e_2}$, where r represents the medical relation, $e_1$ and $e_2$ represent the medical entities, $r(e_1, e_2)$ represents the medical knowledge, Score(•) represents the scoring function, and $M_r$ represents the relation matrix for the medical relation r.

In an alternative embodiment of the present disclosure, the predetermined target function is $$L = \sum_{r(e_1, e_2) \in T} \sum_{r(e'_1, e'_2) \in T'} \max\{\text{Score}(r(e'_1, e'_2)) - \text{Score}(r(e_1, e_2)) + 1, 0\},$$

where L represents the target function, T represents a set of the correct medical knowledges, T' represents a set of the wrong medical knowledges, and $M_r$ represents the relation matrix for the medical relation r.

In an alternative embodiment of the present disclosure, the inference rule finder is further configured to: select a plurality of groups of medical relations from all the medical relations, and create a plurality of to-be-validated inference rules, each of the plurality of to-be-validated inference rule corresponding to one group of medical relations, each group of medical relations including three medical relations; calculate a similarity between a product of relation matrices for two medical relations in each group of medical relations and a relation matrix for the other medical relation in the group of medical relations; and select parts of the to-be-validated inference rules as the final inference rules in accordance with the similarities.

In an alternative embodiment of the present disclosure, the inference rule finder is further configured to: rank the similarities corresponding to all the groups of medical relations and obtain a predetermined number of to-be-validated inference rules having the largest similarity; and determine a predetermined number of to-be-validated inference rules having the largest similarity as the final inference rules.

In an alternative embodiment of the present disclosure, the three medical relations in each group of medical relations meet the following conditions: (1) $L_p \cap H_q \neq \emptyset$, (2)

$H_p \cap H_r \neq \emptyset$ and (3) $L_q \cap r_r \neq \emptyset$, where $H_p$, $H_q$ and $H_r$ represent sets of all first medical entities in triplets corresponding to the three medical relations p, q and r in the group of medical relations respectively, and $L_p$, $L_q$ and $L_r$ represent sets of all second medical entities in the triplets corresponding to the three medical relations p, q and r in the group of medical relations respectively.

In an alternative embodiment of the present disclosure, the inference rule finder is further configured to calculate an L2 norm between the product of the relation matrices for two medical relations in each group of medical relations and the relation matrix for the other medical relation in the group of medical relations as the similarity.

In another aspect, the present disclosure provides in some embodiments a data retrieval method for a medical knowledge base, including: acquiring a relation matrix for each medical relation, the relation matrix representing a relationship between vectors of two medical entities having the medical relation, the medical knowledge base including a plurality of medical knowledges, each medical knowledge comprising two medical entities and one medical relation between the two medical entities; acquiring inference rules in accordance with the relation matrices for the plurality of medical relations, each inference rule including a first medical relation, a second medical relation and a third medical relation, the inference rule representing that the third medical relation is inferred from the first medical relation and the second medical relation; inputting a search word or search pattern; performing a search operation in accordance with the inference rule using the search word or search pattern, so as to acquire the medical knowledge related to the search word or search pattern; and outputting the medical knowledge related to the search word or search pattern.

In an alternative embodiment of the present disclosure, the outputting the medical knowledge related to the search word or search pattern includes displaying the medical knowledge related to the search word or search pattern.

In another aspect, the present disclosure provides in some embodiments a medical knowledge database, including: a data inputting device configured to input therethrough medical knowledge data; a relation matrix learner configured to acquire a relation matrix for each medical relation, the relation matrix representing a relationship between vectors of medical entities having the medical relation, the medical knowledge base including a plurality of medical knowledges, each medical knowledge comprising two medical entities and one medical relation between the two medical entities; an inference rule finder configured to acquire the inference rules in accordance with the relation matrices for the plurality of medical relations, each inference rule including a first medical relation, a second medical relation and a third medical relation, the inference rule representing that the third medical relation is inferred from the first medical relation and the second medical relation; an inputting device configured to input therethrough a search word or search pattern; a searcher configured to perform a search operation in accordance with the inference rule using the search word or search pattern, so as to acquire the medical knowledge related to the search word or search pattern; and an outputting device configured to output the medical knowledge related to the search word or search pattern.

In an alternative embodiment of the present disclosure, the outputting device is further configured to display the medical knowledge related to the search word or search pattern.

BRIEF DESCRIPTION OF THE DRAWINGS

In order to illustrate the technical solutions of the present disclosure or the related art in a clearer manner, the drawings desired for the present disclosure or the related art will be described hereinafter briefly. Obviously, the following drawings merely relate to some embodiments of the present disclosure, and based on these drawings, a person skilled in the art may obtain the other drawings without any creative effort.

DETAILED DESCRIPTION

In order to make the objects, the technical solutions and the advantages of the present disclosure more apparent, the present disclosure will be described hereinafter in a clear and complete manner in conjunction with the drawings and embodiments. Obviously, the following embodiments merely relate to a part of, rather than all of, the embodiments of the present disclosure, and based on these embodiments, a person skilled in the art may, without any creative effort, obtain the other embodiments, which also fall within the scope of the present disclosure.

For a conventional method for automatically discovering medical knowledge, it is necessary to define an inference rule artificially. For example, an inference rule "containing (A, B)^ treating (B, C)=>preventing (A, C)" is defined artificially. Based on the facts that needle mushroom contains flammulin and flammulin can be used to treat a cancer, it is able to infer that needle mushroom can treat the cancer in accordance with the above-mentioned inference rule. However, there is currently a huge number of information in the medical domain, and it will take a lot of time, labor and financial resources to define the inference rule artificially. In addition, complete medical knowledge data may not be acquired necessarily. In the embodiments of the present disclosure, a medical relation is represented as a matrix, so it is able to automatically discover the inference rules from the huge number of medical knowledge through an operation among the matrices, without any necessity to define the inference rules artificially. As a result, it is able to save the labor, the financial resources and the time. In addition, through a medical knowledge base and a retrieval method created in accordance with the inference rules, it is able for a searcher to acquire the complete medical knowledge data.

An embodiment of the present disclosure provides a method and a system for automatically discovering an inference rule for use in a medical knowledge base, so as to automatically discover the inference rule from the medical knowledge base.

In the embodiments of the present disclosure, the medical knowledge base includes a plurality of medical knowledges, and each medical knowledge comprises two medical entities and one medical relation. Each medical knowledge includes three elements, and a triplet may be used in the embodiments of the present disclosure to represent each medical knowledge. For a triplet r ($e_1$, $e_2$), r represents the medical relation, and $e_1$ and $e_2$ represent the medical entities respectively. For example, for treating (flammulin, cancer), "treating" is a medical relation, and "flammulin" and "cancer" are medical entities, i.e., flammulin can be used to treat a cancer.

In the embodiments of the present disclosure, the medical entities in the medical knowledge base may be represented as vectors.

For example, each medical entity may be represented as a one-hot vector. The "one-hot" vector refers to a vector, in which value of one dimension is 1 and values of other dimensions are 0. When the medical knowledge base includes N medical entities totally, these N medical entities may be ranked in any order. When the medical entity "flammulin" is located at a position i, its "one-hot" vector $x_e$ may be ($a_1$, . . . , $a_i$, . . . , $a_N$), where $$a_j = \begin{cases} 1, \text{ if } j = i \\ 0, \text{ if } j \neq i \end{cases},$$

i.e., an $i^{th}$ element is 1, and the other N−1 elements are 0. Hence, the number of the dimensions of the "one-hot" vector is equal to the total number of the medical entities, and each dimension represents one medical entity. For the "one-hot" vector of each medical entity, merely the dimension corresponding to the medical entity is 1, and the other dimensions are 0. For example, when there are three medical entities {calcium, flammulin and zinc} ranked in an order of 1, 2 and 3, the "one-hot" dimension of each medical entity may have three dimensions, with a dimension of 1 corresponding to the medical entity and the other dimensions of 0. For example, the "one-hot" vector of calcium may be (1, 0, 0).

The "one-hot" vector has N*1 dimensions. The medical knowledge base may include a huge number of medical entities, i.e., N may have a very large value. When each medical entity is represented by a "one-hot" vector, there may exist a huge number of one-hot vectors, so it is difficult to treat these one-hot vectors. In addition, some medical entities in the medical knowledge base may have different names but refer to a same or similar medical entity. For example, medical entities "acetaminophen" and "paracetamol" in the medical knowledge base actually refer to a same entity. At this time, it is necessary to represent the two medical entities using a same or similar vector.

In the embodiments of the present disclosure, a high-dimensional "one-hot" vector may be mapped to a low-dimensional vector, so as to reduce the dimensions of the vector effectively, and represent a same or similar medical entity using a same or similar vector.

For example, when a mapping matrix W is a vector having K*N dimensions (where K is a positive integer smaller than N), a vector $y_e$ of a medical entity e may be represented as $y_e = \sigma(Wx_e)$ where σ represents a sigmoid function, $x_e$ represents a "one-hot" vector of the medical entity e, $\sigma(x) = 1/(1+e^{-x})$, and e in σ(x) is a constant. Based on the above equation for calculating $y_e$, because W is a vector having K*N dimensions and $x_e$ is a vector having N*1 dimensions, $Wx_e$ may be a vector having K*1 dimensions and $y_e$ may be a vector having K*1 dimensions. K is smaller than N, so the vector $y_e$ acquired after the mapping operation has dimensions smaller than those of the "one-hot" dimensions. A value of K may be set in accordance with the practical need, and usually it is far smaller than N. The mapping matrix W may learn a value of each element through a predetermined target function, which will be described hereinafter in more details.

The medical knowledge base may include a plurality of medical relations, e.g., "treating", "preventing" and "containing". In the embodiments of the present disclosure, each medical relation may be represented as a relation matrix $M_r$, which representing a relationship between the vectors of the medical entities having the medical relation. For each medical entity, its "one-hot" vector having N dimensions has been dimensionally reduced into a vector having K dimensions, i.e., all the medical entities have been mapped to a K-dimension space (marked as S), and each relation matrix represents the relationship between the medical entities, so the relation matrix may have K*K dimensions, i.e., each relation matrix includes $K^2$ elements. An element $M_r$ (i,j) in an $i^{th}$ row and a $j^{th}$ column (1≤i,j≤K) represents a relationship between an $i^{th}$ dimension and a $j^{th}$ dimension of the space S. In the embodiments of the present disclosure, the relation matrix $M_r$ may learn a value of each element through the predetermined target function, which will be described hereinafter in more details.

In the embodiments of the present disclosure, the inference rule may be discovered through the operation among the relation matrices for the medical relations. To be specific, a product of the relation matrices for any two of the medical relations may be acquired, and then a similarity between the product and the relation matrix for the remaining medical relation may be calculated. When the product is similar to the relation matrix for the remaining medical relation, it is able to acquire the inference rule among the three medical relations.

Figure 1:
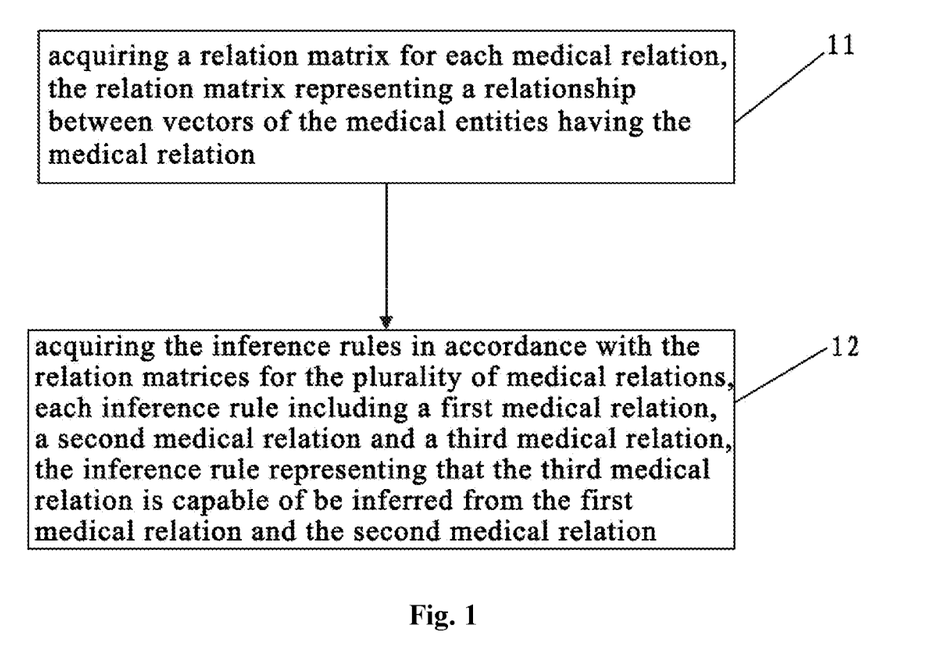
FIG. 1 is a flow chart of a method for automatically discovering an inference rule according to one embodiment of the present disclosure.

Referring to FIG. 1, the present disclosure provides in some embodiments a method for automatically discovering an inference rule for use in a medical knowledge base. The medical knowledge base includes a plurality of medical knowledges, and each medical knowledge comprises two medical entities and one medical relation. The method includes: Step 11, acquiring a relation matrix for each medical relation, the relation matrix representing a relationship between vectors of the medical entities having the medical relation; and Step 12, acquiring the inference rules in accordance with the relation matrices for the plurality of medical relations, each inference rule including a first medical relation, a second medical relation and a third medical relation, the inference rule representing that the third medical relation is inferred from the first medical relation and the second medical relation.

The resultant inference rule is the first medical relation ˆ the second medical relation=>the third medical relation.

In the embodiments of the present disclosure, each medical relation is represented as a matrix, and through an operation among the matrices, the inference rule may be automatically discovered from a huge number of medical knowledge without any necessity to define the inference rule artificially. As a result, it is able to save the labor, the financial resources and the time.

In an alternative embodiment of the present disclosure, the first medical relation $r_1$, the second medical relation $r_2$ and the third medical relation $r_3$ may meet the following conditions (1) $L_{r_1} \cap H_{r_2} \neq \emptyset$, (2) $H_{r_1} \cap H_{r_3} \neq \emptyset$, and (3) $L_{r_2} \cap L_{r_3} \neq \emptyset$, where $H_{r_1}$, $H_{r_2}$ and $H_{r_3}$ represent sets of all first medical entities in triplets corresponding to the first medical relation $r_1$, the second medical relation $r_2$ and the third medical relation $r_3$ respectively, and $L_{r_1}$, $L_{r_2}$ and $L_{r_3}$ represent sets of all second medical entities in the triplets corresponding to the first medical relation $r_1$, the second medical relation $r_2$ and the third medical relation $r_3$.

How to determine the relation matrix for each medical relation will be described hereinafter.

A learning operation may be performed on the relation matrix for each medical relation through the predetermined target function.

In the embodiments of the present disclosure, the predetermined target function is used to optimize the relation matrix for each medical relation in accordance with a score of the medical knowledge corresponding to the medical relation. The learning operation through the predetermined target function is performed so as to enable a score of a correct medical knowledge to be higher than that of a wrong medical knowledge. It should be appreciated that, the medical knowledges in the medical knowledge base have been validated through experiments and experts. In the embodiments of the present disclosure, each medical knowledge in the medical knowledge base is a correct medical knowledge. Any medical knowledge created randomly may be a wrong medical knowledge. For example, a medical knowledge "treating (flammulin, cancer)" in the medical knowledge base is a correct medical knowledge, while a medical knowledge "treating (vitamin A, cancer)" created randomly is a wrong medical knowledge.

Figure 2:
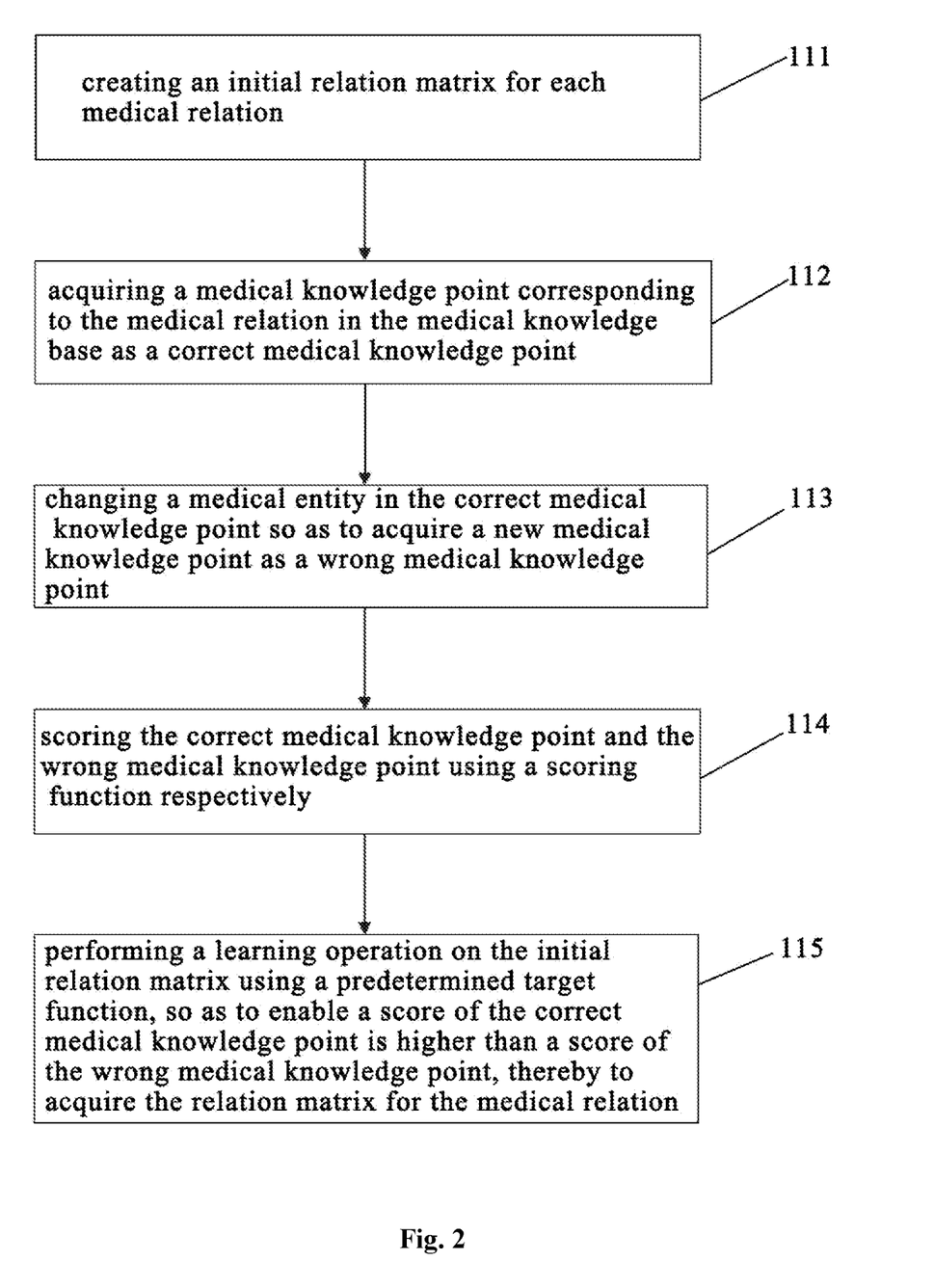
FIG. 2 is a flow chart of the acquisition of a relation matrix for a medical relation according to one embodiment of the present disclosure.

Referring to FIG. 2, the step of acquiring the relation matrix for each medical relation may include the following steps.

Step 111: creating an initial relation matrix for each medical relation. In the initial relation matrix, each element may be of a random value.

Step 112: acquiring a medical knowledge corresponding to the medical relation in the medical knowledge base as a correct medical knowledge. For example, the medical relation "treating" in the medical knowledge base may correspond to a medical knowledge "treating (flammulin, cancer)", "treating (acetaminophen, fever)" and "treating (calamine, itch)".

Step 113: changing a medical entity in the correct medical knowledge to acquire a new medical knowledge as a wrong medical knowledge. For example, an element "flammulin" in the medical knowledge "treating (flammulin, cancer)" may be replaced with "vitamin A", so as to acquire a wrong medical knowledge "treating (vitamin A, cancer)".

Step 114: scoring the correct medical knowledge and the wrong medical knowledge using a scoring function.

Step 115: performing a learning operation on the initial relation matrix using a predetermined target function, so as to enable a score of the correct medical knowledge is higher than a score of the wrong medical knowledge, thereby to acquire the relation matrix for the medical relation.

In the embodiments of the present disclosure, based on a principle where the score of the correct medical knowledge is higher than the score of the wrong medical knowledge, it is able to perform the learning operation on the relation matrix for each medical relation through the predetermined target function in a simple and effective manner.

In an alternative embodiment of the present disclosure, a difference between the number of the correct medical knowledges and the number of the wrong medical knowledges is smaller than a predetermined threshold when the learning operation is performed on the initial relation matrix. In another possible embodiment of the present disclosure, the number of the correct medical knowledges is equal to the number of the wrong medical knowledges. In other words, when the learning operation is performed on the initial relation matrix, the number of the correct medical knowl-edges may be the same, or substantially the same, as the number of the wrong medical knowledges, so as to provide a correct learning result.

In an alternative embodiment of the present disclosure, each medical knowledge may be scored using the following scoring function $\text{Score}(r(e_1, e_2)) = y_{e_1}^T M_r y_{e_2}$, where $r$ represents the medical relation, $e_1$ and $e_2$ represent the medical entities, $r(e_1, e_2)$ represents the medical knowledge, $\text{Score}(\bullet)$ represents the scoring function, and $M_r$ represents the relation matrix for the medical relation $r$.

In some other embodiments of the present disclosure, any other scoring function may also be used.

In an alternative embodiment of the present disclosure, the learning operation may be performed on the relation matrix for each medical relation through the following target function.

$$L = \sum_{r(e_1, e_2) \in T} \sum_{r(e_1', e_2') \in T'} \max\{\text{Score}(r(e_1', e_2')) - \text{Score}(r(e_1, e_2)) + 1, 0\},$$

where $L$ represents the target function, $T$ represents a set of the correct medical knowledges, $T'$ represents a set of the wrong medical knowledges, and $M_r$ represents the relation matrix for the medical relation $r$.

In the embodiments of the present disclosure, a stochastic gradient descent algorithm is used to minimize the predetermined target function, so as to perform the learning operation on the relation matrix for each medical relation. Of course, in some other embodiments of the present disclosure, any other optimization algorithm may also be used.

In the embodiments of the present disclosure, when creating the wrong medical knowledge, e.g., creating the wrong medical knowledge for the medical relation $r$, one medical knowledge $r(e_1, e_2)$, may be selected from the set $T$ of the correct medical knowledges. One medical entity in $r(e_1, e_2)$ may remain the same, while the other medical entity may be replaced. For example, $e_1$ may remain the same and $e_2$ may be replaced with $e'$ randomly, so as to create the set $T'$ of the wrong medical knowledges.

In other words, in the embodiments of the present disclosure, when changing the medical entities for the correct medical knowledge corresponding to the medical relation, any medical entity of the correct medical knowledge may be randomly replaced with another medical entity, so as to acquire the wrong medical knowledge.

The medical knowledge acquired after random replacement is not necessarily wrong, i.e., another correct medical knowledge may probably be acquired. For example, when flammulin in the correct medical knowledge "treating (flammulin, cancer)" is replaced with cytarabine, a new medical knowledge "treating (cytarabine, cancer)" may be a correct medical knowledge. However, the so-called wrong medical knowledge in the embodiments of the present disclosure is in a statistical sense, i.e., most of the medical knowledges acquired randomly are wrong. For example, when the medical knowledge base includes 100000 medical entities, there are relatively few of medical entities for the treatment of cancers, e.g., 1000 medical entities. After random replacement, a probability of the correct medical knowledge is merely 1000/100000=1%, while a probability of the wrong medical knowledge is 99%. When the replacement is performed many times, e.g., 10000 times, based on a law of large numbers, 99% of the results acquired after the 10000 times of replacement are wrong, and no significant influence may be caused even when a very small amount of the results are correct.

In an alternative embodiment of the present disclosure, when changing the medical entity in the correct medical knowledge corresponding to the medical relation, the medical entity in the correct medical knowledge may be replaced with a medical entity other than medical entities in all the correct medical knowledges corresponding to the medical relation, so as to acquire the new medical knowledge as the wrong medical knowledge. For example, all the medical knowledges corresponding to the medical relation "treating" do not include medical entities "needle mushroom" and "ginger", the medical entities in the medical knowledges corresponding to the medical relation "treating" may be replaced with "needle mushroom" or "ginger", and at this time, the probability of the correct medical knowledge may be reduced.

As mentioned above, prior to the learning operation on the relation matrix for each medical relation, it is also necessary to acquire the vector of the medical entity. In the embodiments of the present disclosure, the vector of the medical entity may be acquired through the following steps: acquiring a one-hot code vector for each medical entity through the following formula $$x_e = (a_1, \ldots, a_i, \ldots, a_N), \text{ where } a_j = \begin{cases} 1, \text{ if } j = i \\ 0, \text{ if } j \neq i \end{cases},$$

represents the number of the medical entities in the medical knowledge base, and $x_e$ represents a vector in $N*1$ dimensions; and acquiring a vector of each medical entity in accordance with the one-hot code vector of the medical entity through the following formula $y_e = \sigma(Wx_e)$, where $\sigma(x) = 1/(1+e^x)$, $y_e$ represents a vector in $K*1$ dimensions, W represents a mapping matrix and is a vector in $K*N$ dimensions, and K is a predetermined value smaller than N.

Each element in an initial matrix of the mapping matrix W may be of a random value. Based on the predetermined target function, the final mapping matrix W may also be acquired when the relation matrix is acquired through learning.

A principle of automatically discovering the inference rule will be described hereinafter.

The vector of each medical entity may be normalized into a unit vector (i.e., a vector having a modulus of 1). For any medical entity, $\|e\|=1$, where $\|\cdot\|$ represents a length, i.e., a Euclidean distance. In the same time, the vector $y_{e_1}^T M_{r_1}$ may also be normalized into a unit vector.

After the vector $y_{e_1}^T M_{r_1}$ and the entity vector $y_{e_2}$ have been normalized into the unit vectors, $y_{e_1}^T M_{r_1} y_{e_2}$ may represent a cosine value of an angle between the vectors $y_{e_1}^T M_{r_1}$ and $y_{e_2}$. Based on the predetermined target function, the score of the correct medical knowledge needs to be at least higher than the score of the wrong medical knowledge by 1. At this time, the larger the value of $y_{e_1}^T M_{r_1} y_{e_2}$, the better. However, a maximum value of the cosine value is 1, so one result caused by the optimization of the predetermined target function lies in that the score of the correct medical knowledge may approach to 1, i.e., $y_{e_1}^T M_{r_1} y_{e_2} \approx 1$. Hence, for the correct medical knowledge $r_1$ ($e_1$, $e_2$), $y_{e_1}^T M_{r_1} y_{e_2} \approx 1$.

Because $y_{e_2}$ is normalized into the unit vector, $y_{e_2}^T y_{e_2} \approx 1$. Because $y_{e_1}^T M_{r_1} y_{e_2} \approx 1$ and $y_{e_1}^T M_{r_1}$ is also the unit vector after normalization, $y_{e_1}^T M_{r_1} \approx y_{e_2}^T$. Intuitively, merely a cosine value of the angle between any non-zero unit vector and the unit vector, which is the same as it, is 1.

Identically, for the correct medical knowledge $r_2$ ($e_2$, $e_3$), $y_{e_2}^T M_{r_2} \approx y_{e_3}^T$, so $y_{e_1}^T (M_{r_1} M_{r_2}) \approx y_{e_3}^T$. Because $r_3$ ($e_1$, $e_3$) is tenable, $y_{e_1}^T M_{r_3} \approx y_{e_3}^T$ and $M_{r_1} M_{r_2} \approx M_{r_3}$. In other words, for the medical relations $r_1$, $r_2$ and $r_3$, when $M_{r_1} M_{r_2} \approx M_{r_3}$, it is able to acquire an inference rule $r_1 \wedge r_2 \Rightarrow r_3$. Identically, for the medical relations $r_4$, $r_5$ and $r_6$, when $M_{r_4} M_{r_5} \approx M_{r_6}$, it is able to acquire an inference rule $r_4 \wedge r_5 \Rightarrow r_6$.

Based on the above analysis, it is able to discover the inference rule through the multiplication among the matrices.

In the embodiments of the present disclosure, when a plurality of inference rules has been acquired, the similarities corresponding to these inference rules may also be ranked, and a predetermined number of inference rules having the largest similarities may be selected as the final inference rules.

In an alternative embodiment of the present disclosure, the step of acquiring the inference rule in accordance with the relation matrix for the medical relation may include: selecting a plurality of groups of medical relations from all the medical relations, and creating a plurality of to-be-validated inference rules, each of the plurality of to-be-validated inference rule corresponding to one group of medical relations, each group of medical relations including three medical relations; calculating a similarity between a product of relation matrices for two medical relations in each group of medical relations and a relation matrix for the other medical relation in the group of medical relations; and selecting parts of the to-be-validated inference rules as the final inference rules in accordance with the similarities.

Figure 3:
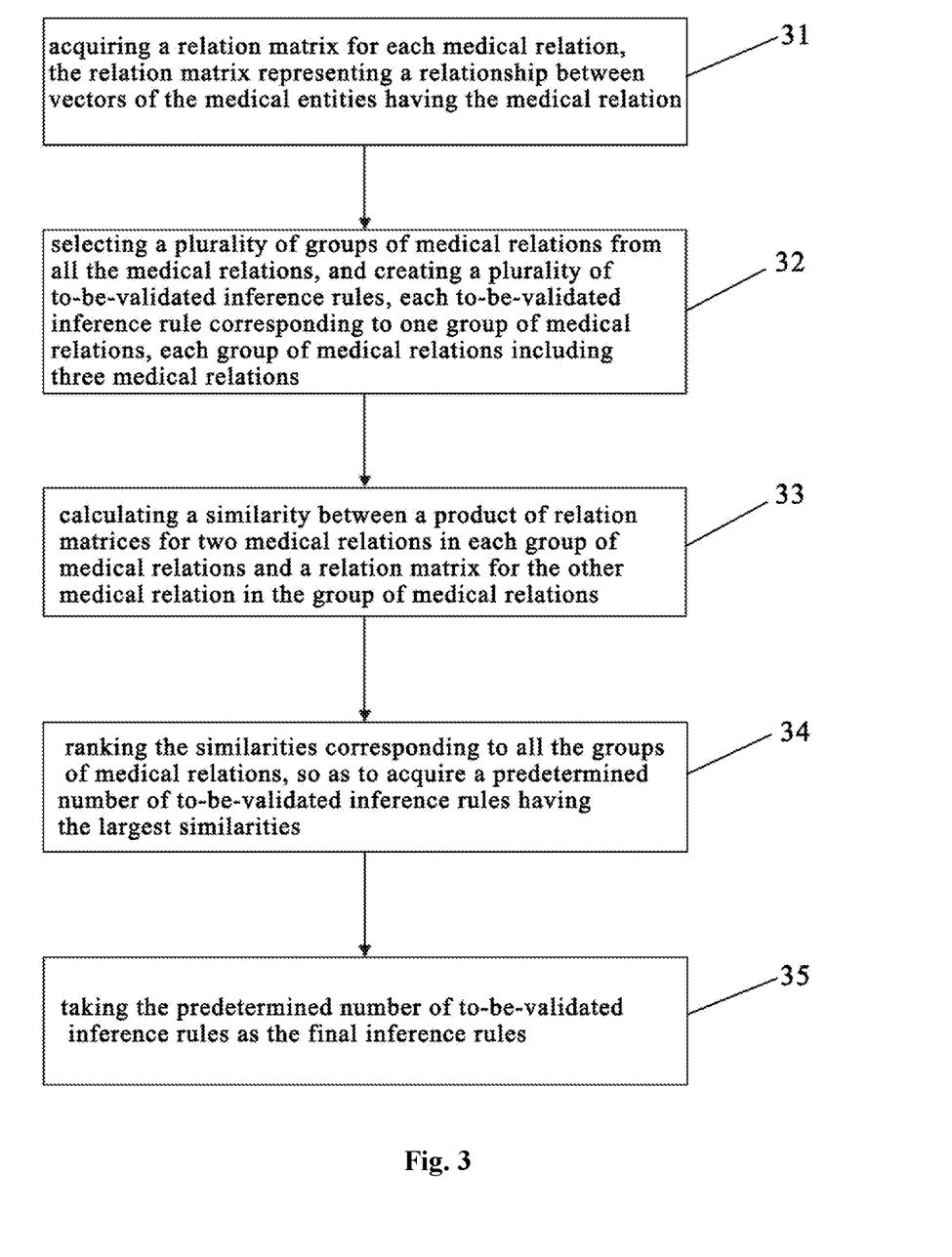
FIG. 3 is another flow chart of the method for automatically discovering an inference rule according to one embodiment of the present disclosure.

Referring to FIG. 3, the present disclosure further provides in some embodiments another method for automatically discovering an inference rule for use in a medical knowledge base. The medical knowledge base includes a plurality of medical knowledges, and each medical knowledge comprises two medical entities and one medical relation. The method includes: Step 31, acquiring a relation matrix for each medical relation, the relation matrix representing a relationship between vectors of the medical entities having the medical relation; Step 32, selecting a plurality of groups of medical relations from all the medical relations, and creating a plurality of to-be-validated inference rules, each of the plurality of to-be-validated inference rule corresponding to one group of medical relations, each group of medical relations including three medical relations; Step 33, calculating a similarity between a product of relation matrices for two medical relations in each group of medical relations and a relation matrix for the other medical relation in the group of medical relations; Step 34, ranking the similarities corresponding to all the groups of medical relations, so as to acquire a predetermined number of to-be-validated inference rules having the largest similarities; and Step 35, taking the predetermined number of to-be-validated inference rules as the final inference rules.

In the embodiments of the present disclosure, the similarities corresponding to all the inference rules are ranked, so as to take the predetermined number of inference rules having the largest similarities as the final inference rules. As a result, it is able to acquire the inference rules in a more correct manner.

Apart from ranking the similarities, the final inference rules may also be selected from the to-be-validated inference rules in any other ways. For example, the to-be-validated inference rules having the similarities greater than a predetermined threshold may be selected as the final inference rules.

In the embodiments of the present disclosure, each of the plurality of to-be-validated inference rule may be created in accordance with any three of all the medical relations.

In an alternative embodiment of the present disclosure, the three medical relations in each group of medical relations meet the following conditions: (1) $L_p \cap H_q \neq \emptyset$, (2) $H_p \cap H_r \neq \emptyset$ and (3) $L_q \cap r_r \neq \emptyset$, where $H_p$, $H_q$ and $H_r$ represent sets of all first medical entities in triplets corresponding to the three medical relations p, q and r in the group of medical relations respectively, and $L_p$, $L_q$ and $L_r$ represent sets of all second medical entities in the triplets corresponding to the three medical relations p, q and r in the group of medical relations respectively.

In an alternative embodiment of the present disclosure, the calculating the similarity between the product of the relation matrices for two medical relations in each group of medical relations and the relation matrix for the other medical relation in the group of medical relations includes calculating an L2 norm between the product of the relation matrices for two medical relations in each group of medical relations and the relation matrix for the other medical relation in the group of medical relations as the similarity.

To be specific, for a triplet $r(e_1, e_2)$ of a given medical relation r, all the medical elements $e_1$ in the triplet form a set $H_r$, and all the medical elements $e_2$ form a set $L_r$. In the embodiments of the present disclosure, a possible inference rule $p \wedge q \Rightarrow r$ may be discovered from medical relation pairs (p,q) which meet the following conditions: (1) $L_p \cap H_q \neq \emptyset$, (2) $H_p \cap H_r \neq \emptyset$ and (3) $L_q \cap L_r \neq \emptyset$. For each medical relation pair (p,q) that meets the above conditions, an L2 norm may be calculated through the formula $\|M_p M_q - M_r\|_2$, and then the medical relation pairs corresponding to the L2 norms may be ranked in an ascending order, where $\|.\|_2$ represents the L2 norm of a matrix. Then, the medical relation pairs (p,q) corresponding to a predetermined number of L2 norms having the largest value may be selected, so as to acquire the inference rule $p \wedge q \Rightarrow r$.

Figure 4:
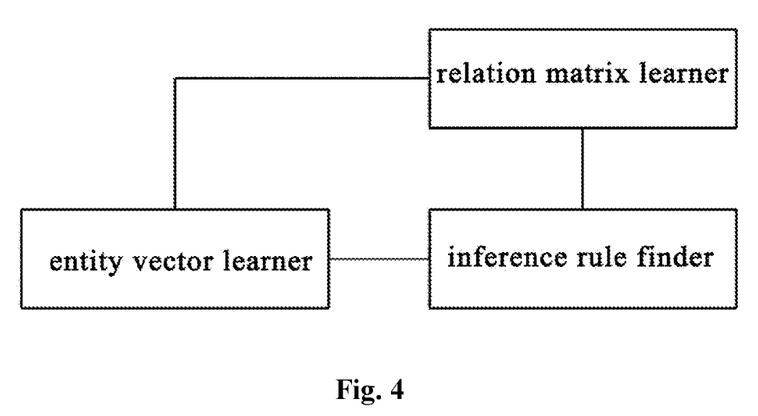
FIG. 4 is a block diagram of a system for automatically discovering an inference rule according to one embodiment of the present disclosure.

Based on an identical inventive concept, referring to FIG. 4, the present disclosure further provides in some embodiments a system for automatically discovering an inference rule for use in a medical knowledge base, the medical knowledge base including a plurality of medical knowledges, each medical knowledge comprising two medical entities and one medical relation, the system including: a relation matrix learner configured to acquire a relation matrix for each medical relation, the relation matrix representing a relationship between vectors of the medical entities having the medical relation; and an inference rule finder configured to acquire the inference rules in accordance with the relation matrices for the plurality of medical relations, each inference rule including a first medical relation, a second medical relation and a third medical relation, the inference rule representing that the third medical relation is inferred from the first medical relation and the second medical relation.

In the embodiments of the present disclosure, each medical relation is represented as a matrix, and through an operation among the matrices, the inference rule may be automatically discovered from a huge number of medical knowledge without any necessity to define the inference rule artificially. As a result, it is able to save the labor, the financial resources and the time.

In an alternative embodiment of the present disclosure, the relation matrix learner is further configured to: create an initial relation matrix for each medical relation; acquire a medical knowledge corresponding to the medical relation in the medical knowledge base as a correct medical knowledge; change a medical entity in the correct medical knowledge so as to acquire a new medical knowledge as a wrong medical knowledge; score the correct medical knowledge and the wrong medical knowledge using a scoring function; and perform a learning operation on the initial relation matrix using a predetermined target function, so as to enable a score of the correct medical knowledge is higher than a score of the wrong medical knowledge, thereby to acquire the relation matrix for the medical relation.

In an alternative embodiment of the present disclosure, a difference between the number of the correct medical knowledges and the number of the wrong medical knowledges is smaller than a predetermined threshold when the learning operation is performed on the initial relation matrix.

In an alternative embodiment of the present disclosure, the relation matrix learner is further configured to replace the medical entity in the correct medical knowledge with a medical entity other than medical entities in all the correct medical knowledges corresponding to the medical relation, so as to acquire the new medical knowledge as the wrong medical knowledge.

In an alternative embodiment of the present disclosure, the system further includes an entity vector learner configured to: acquire a one-hot code vector for each medical entity through the following formula $$x_e = (a_1, \ldots, a_i, \ldots, a_N), \text{ where } a_j = \begin{cases} 1, \text{ if } j = i \\ 0, \text{ if } j \neq i \end{cases},$$

N represents the number of the medical entities in the medical knowledge base, and $x_e$ represents a vector in N*1 dimensions; and acquire a vector of each medical entity in accordance with the one-hot code vector of the medical entity through the following formula $y_e = \sigma(W x_e)$, where $\sigma(x) = 1/(1+e^x)$, $y_e$ represents a vector in K*1 dimensions, W represents a mapping matrix and is a vector in K*N dimensions, and K is a predetermined value smaller than N.

The above embodiments may be implemented in the form of hardware, software or a combination thereof. For example, the methods, steps and functional units described in the embodiments of the present disclosure may be implemented through a processor (a broadly-defined processor, including Central Processing Unit (CPU), processing unit, Application Specific Integrated Circuit (ASIC), logic unit or programmable logic array). The procedures, methods and functional modules described in the embodiments of the present disclosure may be implemented through a separate processor or a plurality of processors. The processor involved in the embodiments or claims of the present disclosure shall be understood as one or more processors. In addition, the above embodiments may be implemented in the form of a software product. The software product is stored in a nonvolatile storage medium and includes a series of instructions, so as to enable a computer device (e.g., a personal computer, a server, or a network device such as router, switch or access point) to execute the method in the embodiments of the present disclosure. The involved relation matrix learner, inference rule finder and entity vector learner may be implemented through the above processors (including a CPU, a memory and a bus). Computer-readable instructions involved in the embodiments of the present disclosure may be stored in a computer-readable storage medium, e.g., a hard disc, a Compact Disc Read-Only Memory (CD-ROM), a Digital Video Disc (DVD), an optical disc, a soft disc, a magnetic tape, a Random Access Memory (RAM), a ROM, or any other appropriate storage device. Also, at least parts of the computer-readable instructions may be replaced with hardware, e.g., custom integrated circuit, gate array, Field Programmable Gate Array (FPGA), Programmable Logic Device (PLD) or a computer having a specific function.

In an alternative embodiment of the present disclosure, the scoring function is $\text{Score}(r(e_1, e_2)) = y_{e_1}^T M_r y_{e_2}$, where r represents the medical relation, $e_1$ and $e_2$ represent the medical entities, $r(e_1, e_2)$ represents the medical knowledge, Score(•) represents the scoring function.

In an alternative embodiment of the present disclosure, the predetermined target function is $$L = \sum_{r(e_1, e_2) \in T} \sum_{r(e'_1, e'_2) \in T'} \max\{\text{Score}(r(e'_1, e'_2)) - \text{Score}(r(e_1, e_2)) + 1, 0\},$$

where L represents the target function, T represents a set of the correct medical knowledges, T' represents a set of the wrong medical knowledges, and $M_r$ represents the relation matrix for the medical relation r.

In an alternative embodiment of the present disclosure, the inference rule finder is further configured to: select a plurality of groups of medical relations from all the medical relations, and create a plurality of to-be-validated inference rules, each of the plurality of to-be-validated inference rule corresponding to one group of medical relations, each group of medical relations including three medical relations; calculate a similarity between a product of relation matrices for two medical relations in each group of medical relations and a relation matrix for the other medical relation in the group of medical relations; and select parts of the to-be-validated inference rules as the final inference rules in accordance with the similarities.

In an alternative embodiment of the present disclosure, the inference rule finder is further configured to: rank the similarities corresponding to all the groups of medical relations and obtain a predetermined amount of to-be-validated inference rules having the largest similarity; and determine a predetermined amount of to-be-validated inference rules having the largest similarity as the final inference rules.

In an alternative embodiment of the present disclosure, the three medical relations in each group of medical relations meet the following conditions: (1) $L_p \cap H_q \neq \emptyset$, (2) $H_p \cap H_r \neq \emptyset$ and (3) $L_q \cap r_r \neq \emptyset$, where $H_p$, $H_q$ and $H_r$ represent sets of all first medical entities in triplets corresponding to the three medical relations p, q and r in the group of medical relations respectively, and $L_p$, $L_q$ and $L_r$ represent sets of all second medical entities in the triplets corresponding to the three medical relations p, q and r in the group of medical relations respectively.

In an alternative embodiment of the present disclosure, the inference rule finder is further configured to calculate an L2 norm between the product of the relation matrices for two medical relations in each group of medical relations and the relation matrix for the other medical relation in the group of medical relations as the similarity.

Figure 6:
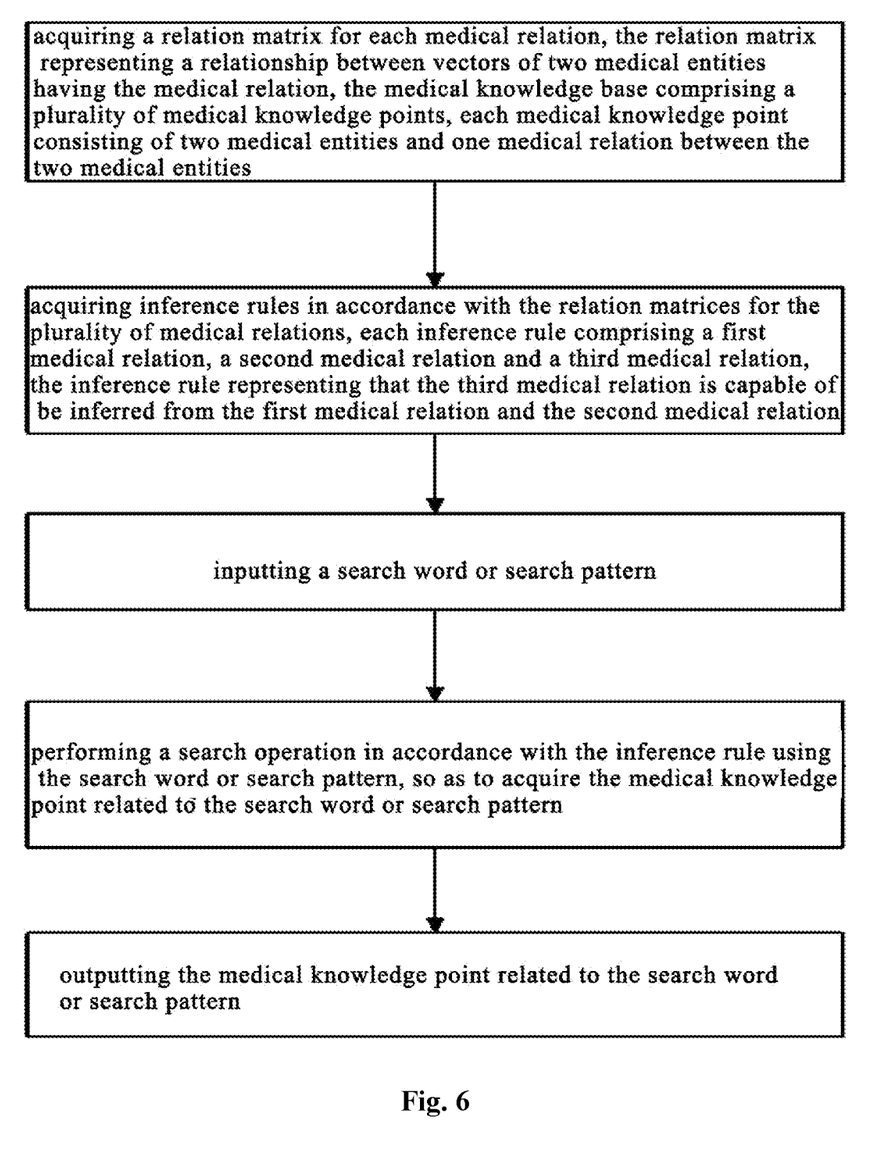
FIG. 6 is a flow chart of a retrieval method according to one embodiment of the present disclosure.

The present disclosure further provides in some embodiments a data retrieval method for a medical knowledge base, including: acquiring a relation matrix for each medical relation, the relation matrix representing a relationship between vectors of two medical entities having the medical relation, the medical knowledge base including a plurality of medical knowledges, each medical knowledge comprising two medical entities and one medical relation between the two medical entities; acquiring inference rules in accordance with the relation matrices for the plurality of medical relations, each inference rule including a first medical relation, a second medical relation and a third medical relation, the inference rule representing that the third medical relation is inferred from the first medical relation and the second medical relation; inputting a search word or search pattern; performing a search operation in accordance with the inference rule using the search word or search pattern, so as to acquire the medical knowledge related to the search word or search pattern; and outputting the medical knowledge related to the search word or search pattern. Procedures of the data retrieval method are shown in FIG. 6.

Figure 5:
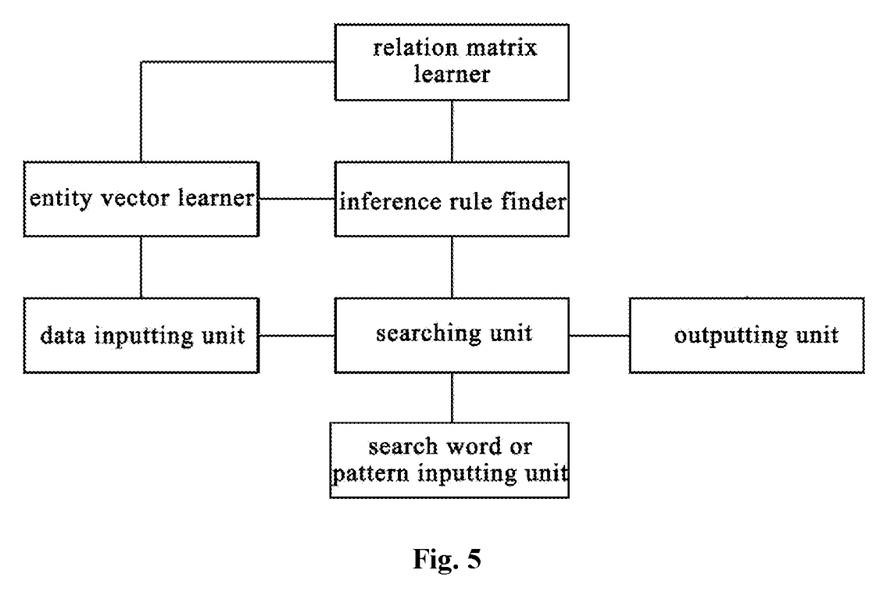
FIG. 5 is a block diagram of a database according to one embodiment of the present disclosure.

The present disclosure further provides in some embodiments a medical knowledge database, including: a data inputting device configured to input therethrough medical knowledge data; a relation matrix learner configured to acquire a relation matrix for each medical relation, the relation matrix representing a relationship between vectors of medical entities having the medical relation, the medical knowledge base including a plurality of medical knowledges, each medical knowledge comprising two medical entities and one medical relation between the two medical entities; an inference rule finder configured to acquire the inference rules in accordance with the relation matrices for the plurality of medical relations, each inference rule including a first medical relation, a second medical relation and a third medical relation, the inference rule representing that the third medical relation is inferred from the first medical relation and the second medical relation; an inputting device configured to input therethrough a search word or search pattern; a searcher configured to perform a search operation in accordance with the inference rule using the search word or search pattern, so as to acquire the medical knowledge related to the search word or search pattern; and an outputting device configured to output the medical knowledge related to the search word or search pattern. A structure of the system is shown in FIG. 5.

In the embodiments of the present disclosure, the data inputting device may be a network inputting device, a Universal Serial Bus (USB) storage device, an optical disc or any other storage device. The inputting device may be a keyboard, a mouse, a camera, a scanner, a light pen, a voice inputting device, a handwriting plate or a touch panel. The searcher may be a conventional one in the medical domain. The outputting device may be a display, a printer, a mapper, a video outputting system, a voice outputting system, or a magnetic recording device.

In the embodiments of the present disclosure, a medical relation is represented as a matrix, so it is able to automatically discover the inference rules from the huge number of medical knowledge through an operation among the matrices, without any necessity to define the inference rules artificially. As a result, it is able to save the labor, the financial resources and the time. In addition, through a medical knowledge base and a retrieval method created in accordance with the inference rules, it is able for a searcher to acquire the complete medical knowledge data.

The above embodiments are for illustrative purposes only, but the present disclosure is not limited thereto. Obviously, a person skilled in the art may make further modifications and improvements without departing from the spirit of the present disclosure, and these modifications and improvements shall also fall within the scope of the present disclosure.

What is claimed is:

1. A computing device implemented method for providing knowledge relations in a knowledge base, the knowledge base comprising a plurality of knowledges, each knowledge comprising two knowledge entities and one knowledge relation between the two knowledge entities, the method comprising:
   determining a relation matrix for each knowledge relation using one or more processors, the relation matrix representing a relationship between vectors of the knowledge entities having the knowledge relation;
   acquiring inference results in accordance with the relation matrices for the plurality of knowledge relations using one or more processors, each inference result comprising a first knowledge relation, a second knowledge relation and a third knowledge relation, the inference results representing that the third knowledge relation is inferred from the first knowledge relation and the second knowledge relation,
   wherein the determining the relation matrix for each knowledge relation comprises:
   providing an initial relation matrix for each knowledge relation;
   acquiring a knowledge corresponding to the knowledge relation in the knowledge base as a correct knowledge;
   changing a knowledge entity in the correct knowledge to acquire a new knowledge as a wrong knowledge;
   scoring the correct knowledge and the wrong knowledge using a scoring function respectively; and
   performing a learning operation on the initial relation matrix using a predetermined target function so that a score of the correct knowledge is higher than a score of the wrong knowledge, and acquiring the relation matrix for the knowledge relation,
   wherein prior to determining the relation matrix for each knowledge relation, the method further comprises:
   acquiring a one-hot code vector for each knowledge entity through the following formula:

$$x_e = (a_1, \ldots, a_i, \ldots, a_N), a_j = \begin{cases} 1, \text{if } j = i \\ 0, \text{if } j \neq i \end{cases},$$

wherein N represents the number of the knowledge entities in the knowledge base, and $x_e$ represents a vector in N*1 dimensions; and
   acquiring a vector of each knowledge in accordance with the one-hot code vector for each knowledge entity through the following formula:

$$y_e = \sigma(Wx_e), \sigma(x) = 1/(1+e^x)$$

wherein $y_e$ represents a vector in K*1 dimensions, W represents a mapping matrix and is a vector in K*N dimensions, and K is a predetermined value smaller than N.

2. The computing device implemented method according to claim 1, wherein a difference between the number of the correct knowledges and the number of the wrong knowledges is smaller than a predetermined threshold when the learning operation is performed on the initial relation matrix.

3. The computing device implemented method according to claim 1, wherein the changing the knowledge entity in the correct knowledge so as to acquire the new knowledge as the wrong knowledge comprises replacing the knowledge entity in the correct knowledge with a knowledge entity other than knowledge entities in all the correct knowledges corresponding to the knowledge relation, so as to acquire the new knowledge as the wrong knowledge.

4. The computing device implemented method according to claim 1, wherein the scoring function is:

$$\text{Score}(r(e_1,e_2)) = y_{e_1}^T M_r y_{e_2}$$

where r represents the knowledge relation, $e_1$ and $e_2$ represent the knowledge entities, $r(e_1, e_2)$ represents the knowledge, Score(•) represents the scoring function, and $M_r$ represents the relation matrix for the knowledge relation r.

5. The computing device implemented method according to claim 4, wherein the predetermined target function is:

$$L = \sum_{r(e_1,e_2) \in T} \sum_{r(e'_1,e'_2) \in T'} \max\{\text{Score}(r(e'_1, e'_2)) - \text{Score}(r(e_1, e_2)) + 1, 0\}$$

where L represents the target function, T represents a set of the correct knowledges, T' represents a set of the wrong knowledges, and $M_r$ represents the relation matrix for the knowledge relation r.

6. The computing device implemented method according to claim 1, wherein the acquiring the inference result in accordance with the relation matrix for the knowledge relation comprises:
   selecting a plurality of groups of knowledge relations from all the knowledge relations, and creating a plurality of to-be-validated inference results, each of the plurality of to-be-validated inference results corresponding to one group of knowledge relations, each group of knowledge relations including three knowledge relations;
   calculating a similarity between a product of relation matrices for two knowledge relations in each group of knowledge relations and a relation matrix for the other knowledge relation in the group of knowledge relations; and
   selecting parts of the to-be-validated inference results as the final inference results in accordance with the similarities.

7. The computing device implemented method according to claim 6, wherein the selecting the parts of the to-be-validated inference results as the final inference results in accordance with the similarities comprises:
   ranking the similarities corresponding to all the groups of knowledge relations and obtaining a predetermined number of to-be-validated inference results having the largest similarity; and
   determining the predetermined number of to-be-validated inference results having the largest similarity as the final inference results.

8. The computing device implemented method according to claim 6, wherein the three knowledge relations in each group of knowledge relations meet the following conditions:

$$L_p \cap H_q \neq \emptyset \quad (1),$$

$$H_p \cap H_r \neq \emptyset, \text{ and} \quad (2)$$

$$L_q \cap r \neq \emptyset \quad (3),$$

where $H_p$, $H_q$ and $H_r$ represent sets of all first knowledge entities in triplets corresponding to the three knowledge relations p, q and r in the group of knowledge relations respectively, and $L_p$, $L_q$ and $L_r$ represent sets of all second knowledge entities in the triplets corresponding to the three knowledge relations p, q and r in the group of knowledge relations respectively.

9. The computing device implemented method according to claim 6, wherein the calculating the similarity between the product of the relation matrices for two knowledge relations in each group of knowledge relations and the relation matrix for the other knowledge relation in the group of knowledge relations comprises calculating an L2 norm between the product of the relation matrices for two knowledge relations in each group of knowledge relations and the relation matrix for the other knowledge relation in the group of knowledge relations as the similarity.

10. The computing device implemented method according to claim 1, wherein the plurality of knowledges are medical knowledges, the knowledge relations are medical relation, and the knowledge entities are medical entities.

11. A computing device implemented system for providing knowledge relations in a knowledge base, the knowledge base comprising a plurality of knowledges, each knowledge comprising two knowledge entities and one knowledge relation, the system comprising:
a processor;
a storage medium containing instructions, which when executed by the processor causes the processor to:
determine a relation matrix for each knowledge relation, the relation matrix representing a relationship between vectors of the knowledge entities having the knowledge relation; and
acquire inference results in accordance with the relation matrices for the plurality of knowledge relations, each inference results comprising a first knowledge relation, a second knowledge relation and a third knowledge relation, the inference results representing that the third knowledge relation is inferred from the first knowledge relation and the second knowledge relation,
wherein the processor is further configured to:
provide an initial relation matrix for each knowledge relation;
acquire a knowledge corresponding to the knowledge relation in the knowledge base as a correct knowledge;
change a knowledge entity in the correct knowledge so as to acquire a new knowledge as a wrong knowledge;
score the correct knowledge and the wrong knowledge using a scoring function respectively;
acquire the relation matrix for the knowledge relation by performing a learning operation on the initial relation matrix using a predetermined target function to enable a score of the correct knowledge higher than a score of the wrong knowledge; and
acquire a one-hot code vector for each knowledge entity through the following formula:

$$x_e = (a_1, \ldots, a_i, \ldots, a_N), a_j = \begin{cases} 1, \text{ if } j = i \\ 0, \text{ if } j \neq i \end{cases}$$

where N represents the number of the knowledge entities in the knowledge base, and $x_e$ represents a vector in N*1 dimensions; and acquire a vector of each knowledge entity in accordance with the one-hot code vector for each the knowledge entity through the following formula:

$$y_e = \sigma(W x_e), \sigma(x) = 1/(1+e^x)$$

where $y_e$ represents a vector in K*1 dimensions, W represents a mapping matrix and is a vector in K*N dimensions, and K is a predetermined value smaller than N.

12. The computing device implemented system according to claim 11, wherein the processor is further configured to make a difference between the number of the correct knowledge and the number of the wrong knowledge smaller than a predetermined threshold when the learning operation is performed on the initial relation matrix.

13. The computing device implemented system according to claim 11, wherein the processor is further configured to acquire the new knowledge as the wrong knowledge by replacing the knowledge entity in the correct knowledge with a knowledge entity other than knowledge entities in all the correct knowledges corresponding to the knowledge relation.

14. The computing device implemented system according to claim 11,
wherein the scoring function is:

$$\text{Score}(r(e_1, e_2)) = y_{e_1}^T M_r y_{e_2}$$

where r represents the knowledge relation, $e_1$ and $e_2$ represent the knowledge entities, $r(e_1, e2)$ represents the knowledge, Score(•) represents the scoring function, and $M_r$ represents the relation matrix for the knowledge relation r,
wherein the predetermined target function is:

$$L = \sum_{r(e_1, e_2) \in T} \sum_{r(e_1', e_2') \in T'} \max\{\text{Score}(r(e_1', e_2')) - \text{Score}(r(e_1, e_2)) + 1, 0\}$$

where L represents the target function, T represents a set of the correct knowledges, T' represents a set of the wrong knowledges, and $M_r$ represents the relation matrix for the knowledge relation r.

15. The computing device implemented system according to claim 11, wherein the plurality of knowledges are medical knowledges, the knowledge relations are medical relation, and the knowledge entities are medical entities.

16. A data retrieval method from a knowledge base, comprising:
acquiring knowledge relations according to the method of claim 1;
inputting a search word or search pattern;
performing a search operation in accordance with the knowledge relations using the search word or search pattern, so as to acquire the knowledge related to the search word or search pattern; and
outputting the knowledge related to the search word or search pattern.

17. A knowledge database, comprises:
a data inputting device configured to input knowledge data;
a relation matrix learner configured to acquire a relation matrix for each knowledge relation, the relation matrix representing a relationship between vectors of knowledge entities having the knowledge relation, the knowledge base comprising a plurality of knowledges, each knowledge comprising two knowledge entities and one knowledge relation between the two knowledge entities;
an inference result finder configured to acquire inference results in accordance with the relation matrices for the plurality of knowledge relations, each inference result comprising a first knowledge relation, a knowledge relation and a third knowledge relation, the inference result representing that the third knowledge relation is inferred from the first knowledge relation and the second knowledge relation;

an inputting device configured to input a search word or search pattern;

a searcher configured to perform a search operation in accordance with the inference result using the search word or search pattern, so as to acquire the knowledge related to the search word or search pattern;

an outputting device configured to output the knowledge related to the search word or search pattern; and optionally an entity vector learner configured to acquire a one-hot code vector for each knowledge entity through the following formula:

$$x_e = (a_1, \ldots, a_i, \ldots, a_N), a_j = \begin{cases} 1, \text{if } j = i \\ 0, \text{if } j \neq i \end{cases}$$

where N represents the number of the knowledge entities in the knowledge base, and $x_e$ represents a vector in N*1 dimensions; and acquire a vector of each knowledge entity in accordance with the one-hot code vector for each knowledge entity through the following formula:

$$y_e = \sigma(W x_e), \sigma(x) = 1/(1+e^x)$$

where $y_e$ represents a vector in K*1 dimensions, W represents a mapping matrix and it is a vector in K*N dimensions, and K is a predetermined value smaller than N.

* * * * *